(12) United States Patent
Curran et al.

(10) Patent No.: US 7,214,819 B2
(45) Date of Patent: May 8, 2007

(54) FLUOROUS TRIPHASIC REACTION AND SEPARATION PROCESSES FOR THE GENERATION OF ENANTIOENRICHED ALCOHOLS, AMINES, CARBOXYLIC ACIDS AND RELATED COMPOUNDS

(75) Inventors: Dennis Patrick Curran, Pittsburgh, PA (US); Zhiyong Luo, San Diego, CA (US)

(73) Assignee: Fluorous Technologies, Inc., Pittsburgh, PA (US)

( * ) Notice: Subject to any disclaimer, the term of this patent is extended or adjusted under 35 U.S.C. 154(b) by 680 days.

(21) Appl. No.: 10/442,664

(22) Filed: May 21, 2003

(65) Prior Publication Data

US 2004/0049071 A1    Mar. 11, 2004

Related U.S. Application Data

(63) Continuation-in-part of application No. 10/094,345, filed on Mar. 8, 2002, now Pat. No. 6,897,331, which is a continuation-in-part of application No. 09/877,944, filed on Jun. 8, 2001, now Pat. No. 6,734,318.

(60) Provisional application No. 60/382,208, filed on May 21, 2002.

(51) Int. Cl.
*C07B 57/00* (2006.01)
(52) U.S. Cl. .................................................. 562/402
(58) Field of Classification Search .................. 562/402
See application file for complete search history.

(56) References Cited

U.S. PATENT DOCUMENTS

| 5,777,121 A | 7/1998 | Curran et al. |
| 5,859,247 A | 1/1999 | Curran et al. |
| 6,156,896 A | 12/2000 | Curran et al. |
| 2003/0003552 A1 | 1/2003 | Theil et al. |
| 2003/0148481 A1 | 8/2003 | Theil et al. |

FOREIGN PATENT DOCUMENTS

| DE | 19963314 | 6/2001 |
| DE | 19963315 | 6/2001 |
| EP | 1321528 | 7/2003 |

OTHER PUBLICATIONS

"Resolution of 1-(2-Naphthyl)ethanol by a Combination of an Enzyme-Catalyzed Kinetic Resolution with a Fluorous Triphasic Separative Reaction" Organic Letters (2002), 4(15), 2585-2587, Luo et al.*
Dennis P. Curran, Strategy-Level Separations in Organic Synthesis: From Planning to Practice, Angew. Chem. Int. Ed. 1998, 37, 1174-1196.
Armido Studer et al., Fluorous Synthesis: A Fluorous-Phase Strategy for Improving Separation Efficiency in Organic Synthesis, Science, vol. 275, Feb. 7, 1997, 823-826.
Armido Studer et al., A Strategic Alternative to Solid Phase Synthesis: Preparation of a Small Isoxazoline Library by "Fluorous Synthesis", Tetrahedron, vol. 53, No. 19, 6681-6696, 1997.
Zhiyong Luo et al., Fluorous Mixture Synthesis: A Fluorous-Tagging Strategy for the Synthesis and Separation of Mixtures of Organic Compounds, Science, vol. 291, Mar. 2, 2001, 1766-1769.
Hiroyuki Nakamura et al., Fluorous Triphasic Reactions: Transportative Deprotection of Fluorous Silyl Ethers with Concomitant Purification, J. Am. Chem. Soc. 2001, 123, 10119-10120.
Dennis P. Curran et al., Thiol additions to acrylates by Fluorous mixture synthesis: relative control of elution order in demixing by the Fluorous tag and the thiol substitutent, Tetrahedron 57, 2001, 5243-5253.
Dennis P. Curran et al., "Experimental techniques in Fluorous synthesis: a user's guide," in Combinatorial Chemistry: A Practical Approach, Oxford University Press, Oxford, 2001, 327-352.
Andre Collet, Resolution of Racemates: Did You Say "Classical"?, Angew. Chem. Int. Ed. 1998, 37, No. 23, 3239-3241.
Istvan T. Horvath, Fluorous Biphase Chemistry, Acc. Chem. Res., 1998, 31, 641-650.
Luis P. Barthel-Rosa et al., Chemistry in Fluorous media: a user's guide to practical considerations in the application of Fluorous catalysts and reagents, Coordination Chemistry Reviews, 190-192 (1999) 587-605.
Jason Eames, Parallel Kinetic Resolutions, Angew. Chem. Int. Ed., 2000, 39, No. 5, 885-888.
Rolf D. Schmid et al., Lipases: Interfacial Enzymes with Attractive Applications, Angew. Chem. Int. Ed., 1998, 37, 1608-1633.
Stanley M. Roberts, Preparative biotransformations: the employment of enzymes and whole-cells in synthetic organic chemistry, J. Chem. Soc., Perkin Trans. 1, 1998, 157-169.
Peter Somfai, Nonenzymatic Kinetic Resolution of Secondary Alcohols, Angew. Chem. Int. Ed. Engl., 1997, 36, No. 24, 2731-2733.

(Continued)

*Primary Examiner*—Samuel Barts
(74) *Attorney, Agent, or Firm*—Kirkpatrick & Lockhart Preston Gates Ellis LLP

(57) ABSTRACT

A method of obtaining an enantioenriched organic compound comprising the steps of: 1) generating from a starting racemic, non-enantiopure or achiral compound a first mixture comprising at least one fluorous-tagged compound and at least one other non-fluorous tagged compound, at least one of these two compounds being enantioenriched relative to the starting compound; 2) contacting a first non-fluorous phase including the first mixture with a fluorous phase at a first phase interface, the fluorous-tagged compound distributing between the first non-fluorous phase and the fluorous phase; and 3) contacting the fluorous phase with a second non-fluorous phase at a second phase interface. The method further includes the step of having a third compound in the second non-fluorous phase that reacts with the fluorous-tagged compound to produce a second compound and the step of generating the first mixture by chemical or enzymatic kinetic resolution of a racemic or non-enantiopure compound.

29 Claims, 4 Drawing Sheets

OTHER PUBLICATIONS

Yun Oliver Long et al., Non-enzymatic Kinetic Resolution of Racemic Alcohols with Chiral Catalysts, Chemtracts-Organic Chemistry, 13:1-8 (2000).

Stanley M. Roberts, Preparative biotransformations, J. Chem. Soc., Perkin Trans., 1, 2000, 611-633.

Benno Hungerhoff et al., Separation of Enantiomers by Extraction Based on Lipase-Catalyzed Enantiomer-Selective Fluorous-Phase Labeling, Angew. Chem. Int. Ed., 2001, 40, No. 13, 2492-2494.

Dennis P. Curran, "Fluorous Techniques for the Synthesis of Organic Molecules: A Unified Strategy for Reaction and Separation," In Stimulating Concepts in Chemistry, Shibasaki, Fraser-Stoddart, Vogtle, eds. Wiley-VCH, New York, 2000, 25-37.

J. N. Murrell et al., Properties of liquids and solutions, Wiley, New York, 1982, 1-3.

Jean Jacques et al., Enantiomers, Racemates, and Resolutions, John Wiley & Sons, New York, 1981,252-405.

Eliel, E. L. et al., Racemization, Stereochemistry of Organic Compounds, Wiley-Interscience, New York, 1994, 297-425.

J. A. Gladysz, Are Teflon "Ponytails" the Coming Fashion for Catalysts?, Science, vol. 266, Oct. 7, 1994, 55-56.

Istvan T. Horvath et al., Facile Catalyst Separation Without Water: Fluorous Biphase Hydroformylation of Olefins, Science, vol. 266, Oct. 7, 1994, 72-75.

Dong-Wei Zhu, A Novel Reaction Medium: Perfluorocarbon Fluids, Synthesis, 953-954, 1993.

Gert E. Berendsen et al., (Heptadecafluorodecyl)dimethylsilyl Bonded Phase for Reversed-Phase Liquid Chromatography, Anal. Chem., 1980, 52, 1990-1993.

Hugo A. H. Billiet et al., Retention and Selectivity Characteristics of a Non-Polar Perfluorinated Stationary Phase for Liquid Chromatography, Journal of Chromatography, 218 (1981) 443-454.

M. Hudlicky, Chemistry of Organic Fluorine Compounds, 2 ed., Ellis Horwood Ltd, West Sussex, England, 1992, 542-545.

B. Boutevin et al., Study of the alkylation of chlorosilanes. Part I. Synthesis of tetra(1H,1H,2H,2H-polyfluoralkyl)silanes, Journal of Fluorine Chemistry, 60 (1993) 211-223.

Curran et al., U.S. Appl. No. 09/506,779, filed Feb. 18, 2000.

Curran et al., U.S. Appl. No. 09/877,944, filed Jun. 8, 2001.

Curran et al., U.S. Appl. No. 10/094,345, filed Mar. 8, 2002.

* cited by examiner

Kinetic Resolution with Fluorous Tagging

Kinetic Resolution with Tag Removed

Desymmetrization with Fluorous Tagging

Product enantiomers are shown arbitrarily and depend on selected chemical or enzymatic reagents.

FLUOROUS TRIPHASIC REACTION AND SEPARATION PROCESSES FOR THE GENERATION OF ENANTIOENRICHED ALCOHOLS, AMINES, CARBOXYLIC ACIDS AND RELATED COMPOUNDS

This application claims priority to, and the benefit of, U.S. Provisional Patent Application Ser. No. 60/382,208, filed on May 21, 2002, incorporated herein by reference, and U.S. Nonprovisional Patent Applications Ser. No. 09/877,944, filed on Jun. 8, 2001, now U.S. Pat. No. 6,734,318 B2, and Ser. No. 10/094,345, filed on Mar. 8, 2002, now U.S. Pat. No. 6,897,331 B2, of which two Nonprovisional Applications the following specification is a Continuation-in-Part.

BACKGROUND OF THE INVENTION

1. Field of the Invention

The present invention relates to fluorous triphasic reaction and separation processes and, especially, to the applications of these processes to the resolution of racemic or partially enantiopure organic compounds such as alcohols, amines, carboxylic acids and derivatives of carboxylic acids.

2. Description of Related Art

Resolutions of racemic organic compounds into their enantioenriched or enantiopure component enantiomers are an important and commonly used process in chemical, pharmaceutical, biotechnological, agricultural and other industries. In the pharmaceutical field, for example, racemic drugs are frowned upon because one enantiomer of a racemate typically predominately or exclusively induces the decided physiological or pharmacological effects. Accordingly, highly enantioenriched or enantiopure drug substances are almost always preferred over racemates.

Highly enantioenriched or enantiopure compounds are generally obtained by one of three basic strategies: 1) they can be prepared from other enantiopure compounds such as natural products by chemical synthesis; 2) they can be prepared from achiral compounds by asymmetric synthesis, or 3) they can be prepared from racemic compounds by resolution. Because many racemic compounds are commercially available or easily prepared, the resolution strategy is especially important. See, for example, J. Jacques, A. Collet, S. H. Wilen, *Enantiomers, Racemates and Resolutions*; Wiley: New York, 1981; E. L. Eliel, S. Wilen, *Stereochemistry of Organic Compounds*; Wiley-Interscience: New York, 1994, Chapter 7; and A. Collet, "Resolution of racemates: Did you say 'classical'?," *Angew. Chem., Int. Ed. Eng.*, 37, 3229 (1998). However, resolutions can often be expensive, wasteful and environmentally unfriendly processes. The problem is especially acute for the general class of resolutions called kinetic resolutions, in which a mixture of a starting compound and a chemical derivative or product must be separated. This separation is often time consuming and expensive, especially when chromatography and related separation processes are used. Such processes often generate large amounts of waste solvent that must be disposed of or destroyed. Improvements in reaction and separation processes are therefore desirable.

Fluorous techniques for chemical synthesis have recently emerged as powerful new reaction and separation tools; see, for example, D. P. Curran, *Stimulating Concepts in Chemistry*; F. Vögtle, J. F. Stoddard and M. Shibasaki, Ed.; Wiley-VCH: New York, 2000, p. 25. Most fluorous techniques can be classified by the separation method employed. Processes such as fluorous biphasic reactions and more recently fluorous triphasic reactions are typical of liquid-liquid based separations. See, for example, I. T. Horvath, "Fluorous biphase chemistry," *Acc. Chem. Res.* 31, 641 (1988). The present inventors have discovered that new fluorous triphasic reaction and separation processes provide powerful and practical new methods for chemical resolution and other processes.

SUMMARY OF THE INVENTION

In one embodiment, the present invention provides a method of obtaining an enantioenriched organic compound, such as a chiral alcohol, amine, carboxylic acid or carboxylic acid derivative compound, comprising the steps of: 1) generating from a first racemic, non-enantiopure or achiral compound a mixture comprising at least one fluorous tagged compound and at least one other non-fluorous tagged compound, at least one of these two compounds being enantioenriched relative to the first compound; 2) contacting a first non-fluorous phase including the mixture with a fluorous phase at a first phase interface, the fluorous-tagged compound distributing between the first non-fluorous phase and the fluorous phase; and 3) contacting the fluorous phase with a second non-fluorous phase at a second phase interface.

In another embodiment, the method includes the step of generating the first mixture by chemical or enzymatic kinetic resolution of a racemic or non-enantiopure chiral alcohol, amine, carboxylic acid or carboxylic acid derivative. The first mixture can be generated, for example, in an independent process and then added to the first non-fluorous phase. It can also be generated in the first non-fluorous phase prior to or concomitant with the fluorous triphasic separation process. The method can also include the step of enantioselective attachment (tagging) or removal (detagging) of a fluorous group onto a precursor compound to synthesize a fluorous-tagged first compound by either chemical or enzymatic means.

In yet another embodiment, the method further includes the step of contacting the second non-fluorous phase with a second fluorous phase at a third phase interface. In this embodiment, the method can also include the step of contacting the second fluorous phase with a third non-fluorous phase at a fourth phase interface. The method can thus include a series of reaction and/or separations as described above and below. The organic compounds of the present invention, which include without limitation alcohols, amines, carboxylic acids and carboxylic acid derivatives, may also be organometallic compounds. Alcohols for derivatization with fluorous tags may be primary, secondary or tertiary, while amines for derivatization may be primary or secondary. Carboxylic acid derivatives are well known to those skilled in the art and include, for example, esters, amides, acid halides, thioesters and the like. All these compounds may contain other functional groups as well in addition to the functional group involved in the enantioenrichment reaction and separation process.

In general, the fluorous phase serves as a barrier to prevent the two non-fluorous phases from mixing, but molecules that can transport, diffuse or migrate through the fluorous phase can pass from one side to the other. As used herein, the term "transport" includes unaided movement, migration or diffusion of a chemical substance or diffusion or migration assisted by a reagent.

The fluorous phase(s) of the present invention can, for example, include any number of fluorous liquids as known in the art, including fluorous solvents. As used herein, the term "fluorous liquid" refers generally to a liquid and/or a liquid mixture that is rich in carbon-fluorine bonds. As used herein, the term "fluorous solvent" refers generally to a solvent and/or a solvent mixture that is rich in carbon-fluorine bonds. Fluorous solvents include fluorocarbons (for example, perfluorohexane and perfluoroheptane), fluorohydrocarbons, fluorinated ethers (for example, perfluorobutyltetrahydrofuran) and fluorinated amines (for example, perfluorotriethyl amine), among others. In general, fluorous liquids and solvents have Hildebrand solubility parameters less than about 14 $MPa^{1/2}$. Many fluorous liquids and solvents are commercially available, and a partial list of commercially available and otherwise known fluorous liquids and solvents is contained in Barthel-Rosa, L. P., Gladysz, J. A., "Chemistry in fluorous media: a user's guide to practical considerations in the application of fluorous catalysts and reagents," *Coord. Chem. Rev.*, 192, 587–605 (1999).

As used herein, the term "liquid" refers generally to phases that take the shape of their container without necessarily filling it (J. N. Murrell, E. A. Boucher, *Properties of Liquids and Solutions*, Wiley: NY, 1982, pp. 1–3). Non-viscous liquids fill a container quickly, while liquid phases with a high viscosity may take a perceptible time to fill a container. Examples of high-viscosity fluorous liquids include, for example, oligomeric mixtures such as the Krytox series available from Dupont.

The term "liquid" also includes supported liquids wherein, for example, the liquid is included in the pore space of a macro-porous or micro-porous support (for example, a liquid membrane). The term "liquid" further includes gel phases, which are formed, for example, by adding a gelling agent to a liquid phase, and plasticized liquid phases. The term "liquid" also includes solutions of nominally pure liquids and other chemical species dissolved in or suspended in them. For example, such dissolved species can be other liquids, solids that form a pseudophase (for example, perfluoroalkane sulfonate of perfluoroalkane carboxylate surfactants which may form reverse micelles or other pseudophases), transport agents or carriers (for example, metal chelators, metal complexes, organic molecular receptors or nanoparticles).

Non-fluorous phases of the present invention can generally be any non-fluorous liquid or solvent as known in the art. As used herein, the terms "non-fluorous liquid" and "non-fluorous solvent" refers generally to organic and aqueous liquids and solvents, respectively, and/or to mixtures thereof. Preferred non-fluorous liquids have a Hildebrand solubility parameter greater than about 17 $MPa^{1/2}$, and more preferred non-fluorous liquids have a Hildebrand parameter greater than about 18 $MPa^{1/2}$. Water and other aqueous liquid mixtures are suitable non-fluorous liquids for use in the present invention, as are many organic liquids including, but not limited to, acetonitrile, ethyl acetate, ethanol, methanol, tetrahydrofuran, dimethyl formamide, dimethyl sulfoxide, toluene and benzene. Non-traditional organic liquids and other neoteric solvents such as ionic liquids can also be used, as can supercritical fluids.

In the methods of the present invention, the fluorous triphasic system preferably does not become substantially homogeneous at any point in the process. In this regard, the fluorous and non-fluorous phases preferably remain substantially immiscible during the course of the process. However, some mixing or miscibility at the phase boundary (interface) between the fluorous and non-fluorous phases is allowable and may even be helpful to promote the contact of the fluorous and non-fluorous phases and thereby facilitate exchange or transport of certain components between the respective phases. Mixing of the fluorous phase with either or both non-fluorous phases can be effected through mechanical, chemical or other means provided that the two non-fluorous phases are not allowed to mix directly with each other.

In addition, the non-fluorous phase may distribute into the fluorous phase altering its composition during a reaction, separation or reaction/separation procedure. Likewise, the fluorous phase may distribute into the non-fluorous phase, altering its composition. The conditions for miscibility or immiscibility of many fluorous and non-fluorous liquids and liquid mixtures are well known, and unknown pairings can often be predicted by differences in Hildebrand solubility parameters or can be readily determined experimentally.

In many embodiments, the first non-fluorous phase includes at least one compound other than the fluorous-tagged compound. The other compound could be the starting alcohol, amine carboxylic or carboxylic acid derivative or a derivative therefrom, and it has a distribution coefficient less than the fluorous-tagged compound and preferably distributes preferentially into the first non-fluorous phase. The higher distribution coefficient of the fluorous-tagged compound (for example, as a result of increased or greater fluorous nature of the compound) as compared to the other compound(s) results in a separation of the fluorous-tagged compound from the other compound(s) before and/or during the reaction step without a separate separation step/apparatus.

Preferably, the fluorous-tagged compound has a distribution coefficient between approximately 0.01 and approximately 10 (as determined between the first fluorous phase and the first non-fluorous phase). More preferably, the fluorous-tagged compound has a distribution coefficient between approximately 0.1 and approximately 5.0. Most preferably, the fluorous-tagged compound has a distribution coefficient between approximately 0.5 and approximately 2.0.

As used herein, the distribution coefficient ($K_D$) is defined generally as the total concentration of a substance (for example, a molecule, molecular fragment, compound, ion, or complex) in the fluorous phase divided by the total concentration of the substance in the non-fluorous phase, at equilibrium. An experimental measurement of the concentration of a substance at equilibrium with two immiscible liquid phases yields the distribution coefficient. If that substance does not participate in chemical or physical equilibria other than partitioning, then the distribution coefficient is the same as the partition coefficient. The partition coefficient reflects the relative tendency of the substance to dissolve in each of the two immiscible phases at equilibrium. If that substance enters into other chemical or physical equilibria, for example protonation/deprotonation, metal binding/chelation, association with a receptor, micellization, etc., then the distribution coefficient represents the net effect of all of the equilibria, namely, the partitioning equilibria and all other chemical and physical equilibria in which the substance takes part. In cases where an equilibrium is not reached, for example, as a result of an ongoing chemical reaction that continually displaces the equilibrium, the measurement of a distribution coefficient may not be practical, and experiments to measure the relative concentrations of a substance instead provide an operational non-equilibrium distribution ratio.

In general, a substance that distributes preferentially into the fluorous phase has a distribution coefficient greater than 1 (and often much greater than 1), and a substance that distributes preferentially into a non-fluorous phase (for example, an organic phase) has a distribution coefficient less than 1 (and often much less than 1).

To effect separation, the distribution coefficient(s) of one or more compounds other than the fluorous-tagged compound (as measured between the first fluorous phase and the first non-fluorous phase) in the methods of the present invention are less than the distribution coefficient of the fluorous-tagged compound, resulting in faster transport of the fluorous-tagged compound through the first fluorous phase. These other compounds can include, for example, a third compound which is added to the second non-fluorous phase and which reacts with the fluorous tagged compound to produce a second compound. The third compound can be, for example, an organic, organometallic or inorganic reagent, reactant or catalyst that is added to cleave a portion or all of the fluorous tag from the fluorous-tagged compound to generate the second compound. In some cases, photolysis, heating or other treatment of the second non-fluorous phase can induce formation of the second compound without addition of a third compound. The second compound could, for example, be an enantioenriched version of the first compound, or a derivative thereof.

The distribution coefficient(s) of other compound(s), for example the second and third compounds, are preferably no greater than two times less than (or no greater than ½ of) the distribution coefficient of the fluorous-tagged compound. More preferably, the distribution coefficient(s) of other compound(s) are no greater than five times less than (or no greater than ⅕ of) the distribution coefficient of the fluorous-tagged compound. Most preferably, the distribution coefficient(s) of other compound(s) are no greater than ten times less than (or no greater than ¹⁄₁₀ of) the distribution coefficient of the fluorous-tagged compound.

Likewise, the distribution coefficient(s) of the second compound and other product compounds (as measured between the first fluorous phase and the second non-fluorous phase) in the methods of the present invention are less than the distribution coefficient of the fluorous-tagged compound (as measured between the first fluorous phase and the first non-fluorous phase) to minimize back transport of the second compound through the first fluorous phase. The distribution coefficients of the second compound and any other product compound are preferably no greater than two times less than (or no greater than ½ of) the distribution coefficient of the fluorous-tagged compound. More preferably, the distribution coefficient of the second compound is no greater than five times less than (or no greater than ⅕ of) the distribution coefficient of the fluorous-tagged compound. Most preferably, the distribution coefficient of the second compound is no greater than ten times less than (or no greater than ¹⁄₁₀ of) the distribution coefficient of the fluorous-tagged compound.

The first mixture of the non-fluorous compound and the fluorous compound can be generated, for example, by chemical or enzymatic attachment of a fluorous tag to a suitable achiral, racemic or enantioenriched alcohol, amine, carboxylic acid or carboxylic acid derivative compound. For example, the mixture can be generated by chemical or enzymatic kinetic resolution of a racemate or an enantioenriched mixture of enantiomers. In that case, the non-fluorous component of the mixture is typically an enantioenriched version of one of the enantiomers of the original compound and the fluorous-tagged component is an enantioenriched derivative of the other enantiomer. The mixture of the fluorous component and the non-fluorous component can also be generated, for example, by chemical or enzymatic parallel kinetic resolution (sometimes called PKR). In that case, the non-fluorous component is typically an enantioenriched non-fluorous derivative of one of the enantiomers of the first compound while the fluorous component is an enantioenriched fluorous-tagged derivative of the other enantiomer. The mixture of the non-fluorous compound and the fluorous compound can also be generated by chemical or enzymatic desymmetrization of an achiral compound, for example, a meso compound. In this case, the fluorous-tagged component is an enantioenriched, desymmetrized derivative, while the non-fluorous component is typically the starting achiral compound.

All of these processes, as well as other processes for asymmetric derivatization that can be adopted for fluorous tagging or detagging, are well known to those skilled in the art. See, for example, J. Eames, "Parallel kinetic resolutions, "*Angew. Chem., Int. Ed. Engl.,* 39, 885 (2000); J. Jacques, A. Collet, S. H. Wilen, *Enantiomers, Racemates and Resolutions*, Wiley: New York, 1981; E. L. Eliel, S. Wilen, *Stereochemistry of Organic Compounds*, Wiley-Interscience: New York, 1994, Chapter 7; and A. Collet, "Resolution of racemates: Did you say 'classical'?," *Angew. Chem., Int. Ed. Eng.,* 37, 3239 (1998); R. D. Schmid, R. Verger, "Lipases: Interfacial enzymes with attractive applications," *Angew. Chem., Int. Ed. Engl.,* 37, 1609 (1998); S. M. Roberts, "Preparative biotransformations: the employment of enzymes and whole-cells in synthetic organic chemistry," *J. Chem. Soc., Perkin Trans.,* 1, 157 (1998); P. Somfai, "Non-enzymatic kinetic resolution of secondary alcohols." *Angew. Chem., Int. Ed. Engl.,* 36, 2731 (1997); Y. O. Long, L. A. Paquette, "Non-Enzymatic Kinetic Resolution of Racemic Alcohols with Chiral Catalysts," *Chemtracts: Organic Chemistry,* 13, 1 (2000); S. M. Roberts, "Preparative biotransformations," *J. Chem. Soc., Perkin Trans.,* 1, 611 (2000).

The enantiomeric excess, or "ee," for a given pair of enantiomers is the percentage of the major enantiomer less the percentage of the minor enantiomer. A racemate or racemic mixture is an equal mixture of two enantiomers and therefore has 0% ee. Enantioenriched compounds are mixtures with one enantiomer's being present in excess over the other (ee >0% and <100%). For example, a sample of 40% ee consists of 70% of the major enantiomer and 30% of the minor enantiomer. In the practice of the invention, in the case that the first mixture is racemic or the starting compound is achiral, the enantiopurity of at least one of the non-fluorous compound and the fluorous compound is preferentially greater than about 40% ee. More preferentially it is greater than about 70% ee and most preferentially it is greater than about 85% ee. In the case where the first mixture is already enantioenriched, the ee of at least one of the non-fluorous compound and the fluorous compound is greater than the ee of the first mixture. (Ideally, enantiopure compounds consist of a single enantiomer only. However, in common usage, compounds are often referred to as enantiopure if their ees are above an arbitrarily high limit where the quantification of the minor enantiomer becomes difficult. Often this arbitrary limit is in the vicinity of 99% ee.)

The fluorous-tagged compound can, for example, react with the third compound to produce the second compound, which is less fluorous in nature than the first fluorous-tagged compound. The reaction of the first fluorous-tagged compound and the third compound can also produce a fluorous compound (for example, a fluorous byproduct) which preferably distributes preferentially from the second non-fluorous phase into the fluorous phase, thereby being separated from the second compound which preferably distributes preferentially into the second non-fluorous phase. In general, the fluorous compound or byproduct preferably has a distribution coefficient substantially greater than 1 (as measured between the first fluorous phase and the second non-fluorous phase). More preferably, the fluorous compound or byproduct has a distribution coefficient greater than 3. Most preferably, the fluorous compound or byproduct has a distribution coefficient greater than 10. If the fluorous byproduct or other fluorous products are not separated from the second compound to a sufficient extent, then other fluorous separation techniques (for example, liquid-liquid separation(s) and/or solid-liquid separation(s) can be used to effect separation.

As used herein, the terms "fluorous tagging" or "fluorous-tagged" refers generally to attaching a fluorous moiety or group (referred to as a "fluorous tagging moiety," "fluorous tagging group" or simply "fluorous tag") to a compound to create a "fluorous-tagged compound." Fluorous tags are also sometimes called "fluorous labels," "fluorous phase labels," or "fluorous protecting groups." Preferably, the fluorous tagging moiety is attached via covalent bond. However, other effective attachments such as ionic bonding, chelation or complexation can also be used. Fluorous tagging moieties facilitate separation of fluorous-tagged compounds from other compounds as a result of differences in the fluorous nature of the compounds.

As used herein, the term "fluorous," when used in connection with an organic (carbon-containing) molecule, moiety or group, refers generally to an organic molecule, moiety or group having a domain or a portion thereof rich in carbon-fluorine bonds (for example, fluorocarbons, fluorohydrocarbons, fluorinated ethers and fluorinated amines). The terms "fluorous-tagged reagent" or "fluorous reagent," thus refer generally to a reagent comprising a portion rich in carbon-fluorine bonds. As used herein, the term "perfluorocarbons" refers generally to organic compounds in which all hydrogen atoms bonded to carbon atoms have been replaced by fluorine atoms. The terms "fluorohydrocarbons" and "hydrofluorocarbons" include organic compounds in which at least one hydrogen atom bonded to a carbon atom has been replaced by a fluorine atom. The attachment of fluorous moieties to organic compounds is discussed for example, in U.S. Pat. No. 5,859,247, and U.S. Pat. No. 5,777,121, which are incorporated herein by reference.

DESCRIPTION OF THE PREFERRED EMBODIMENTS

Although specific examples are provided herein, the present techniques may be applied to a wide variety of organic compounds including without limitation organometallic compounds. The resolution of racemic or non-enantiopure secondary or tertiary alcohols is one among many representative embodiments of this invention. One of two general approaches is typically adopted, as summarized in FIG. 1. In the first, a fluorous tag is attached enantioselectively to a racemic mixture of alcohols. This can be done by using asymmetric chemical or enzymatic methods. In the second, a racemic or non-enantiopure mixture of tagged alcohols is enantioselectively detagged by using chemical or enzymatic methods. Tagging to form an ester group is illustrative, but the formation or cleavage of other derivatives of alcohols, including carbamates, carbonates and urethanes, is also applicable. In either case, a new mixture results in which both the original alcohol and its fluorous-tagged derivative are enantiomerically enriched relative to the starting racemate because of the enantioselective chemical or enzymatic transformation. The enantioselective fluorous tagging or detagging step is typically done before the triphasic separation/reaction but it is sometimes advantageous, especially in detagging reactions, to do the steps of tagging or detagging and triphasic separation/reaction simultaneously.

Figure 1:
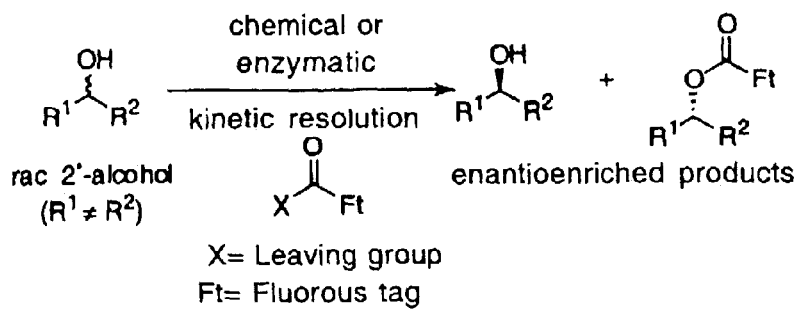
FIG. 1 is a collection of three chemical reaction formula examples of methods to generate enantioenriched, fluorous-tagged alcohols.
Figure 1:
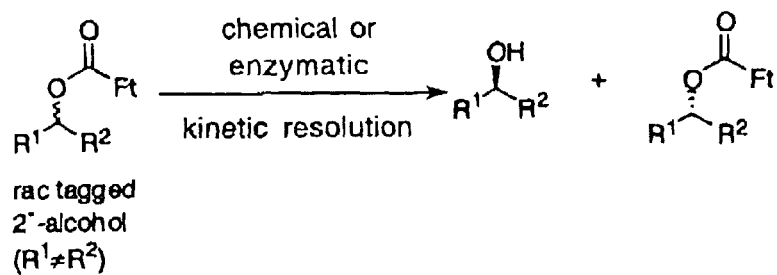
Figure 1:
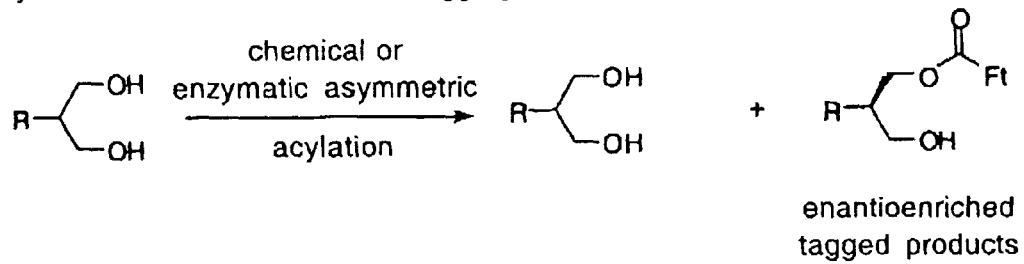

A second representative embodiment of this invention is the desymmetrization of meso compounds. This is also illustrated in FIG. 1 with chemical or enzymatic fluorous tagging of a meso diol.

Figure 2:
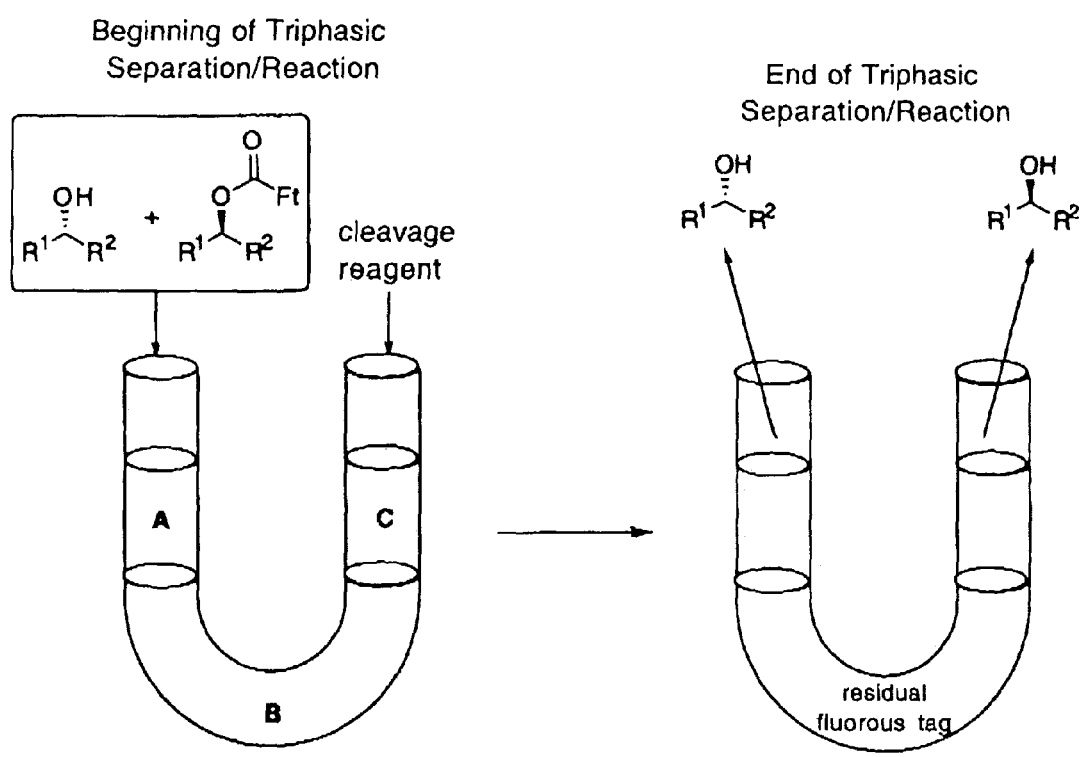
FIG. 2 is a schematic diagram of a triphasic separation/reaction in ester detagging to give enantioenriched alcohols.

The mixture of the alcohol and the fluorous-tagged derivative is then subjected to a fluorous triphasic reaction as illustrated in FIG. 2. The mixture is added to the source side of a triphasic apparatus or reactor containing a non-fluorous solvent (the first non-fluorous phase, typically an organic solvent, sometimes with small amounts of water). A reagent to cleave the fluorous tag from the tagged derivative is added to the receiving side, which contains a second non-fluorous solvent (the second non-fluorous phase) that can be the same as or different from that on the source side. The two non-fluorous phases are prevented from contacting each other by a fluorous phase, which is typically a fluorous solvent such as FC-72 or perfluoromethylcyclohexane. Substantially any order of mixing of the reagents and phases is permissible, provided that the two non-fluorous phases are not allowed to contact each other directly at any time.

Many kinds of reagents are known to those skilled in the art for cleavage of esters, carbamates, urethanes, carbonates and related derivatives, and due to the inertness of fluorous media, substantially any of these can be used as appropriate for removal of the fluorous tag. Common reagents for the deacylation reactions are acids such as sulfuric acid or bases such as alkali hydroxides or alkoxide (for example, NaOH, LiOMe, etc.). The organic or inorganic cleavage reagent preferentially has a low distribution coefficient; that is, it resides substantially in the non-fluorous receiving phase and does not partition efficiently into the fluorous phase. In this way, the detagging reaction takes place predominately in or near the non-fluorous receiving phase and not in or near the non-fluorous source phase. A few reagents, for example gases like HCl and HBr, do not have low distribution coefficients and are therefore not preferred cleavage reagents. The distribution coefficients of many reagents are known or can be readily predicted from known data, or they can be measured by simple experiments as described above.

During the course of the triphasic separation and reaction process, the tagged enantiomer preferentially passes through the fluorous phase and is detagged to provide the corresponding enantiomeric alcohol in the receiving phase. The reaction is terminated after a suitable time to provide alcohol enriched in one enantiomer from the source side and alcohol enriched in the other enantiomer from the receiving side. When the starting material is racemic, both alcohols are enantioenriched compared to the starting material. When the starting material is not racemic, at least one of the product alcohols is enantioenriched relative to the starting material.

Figure 3:
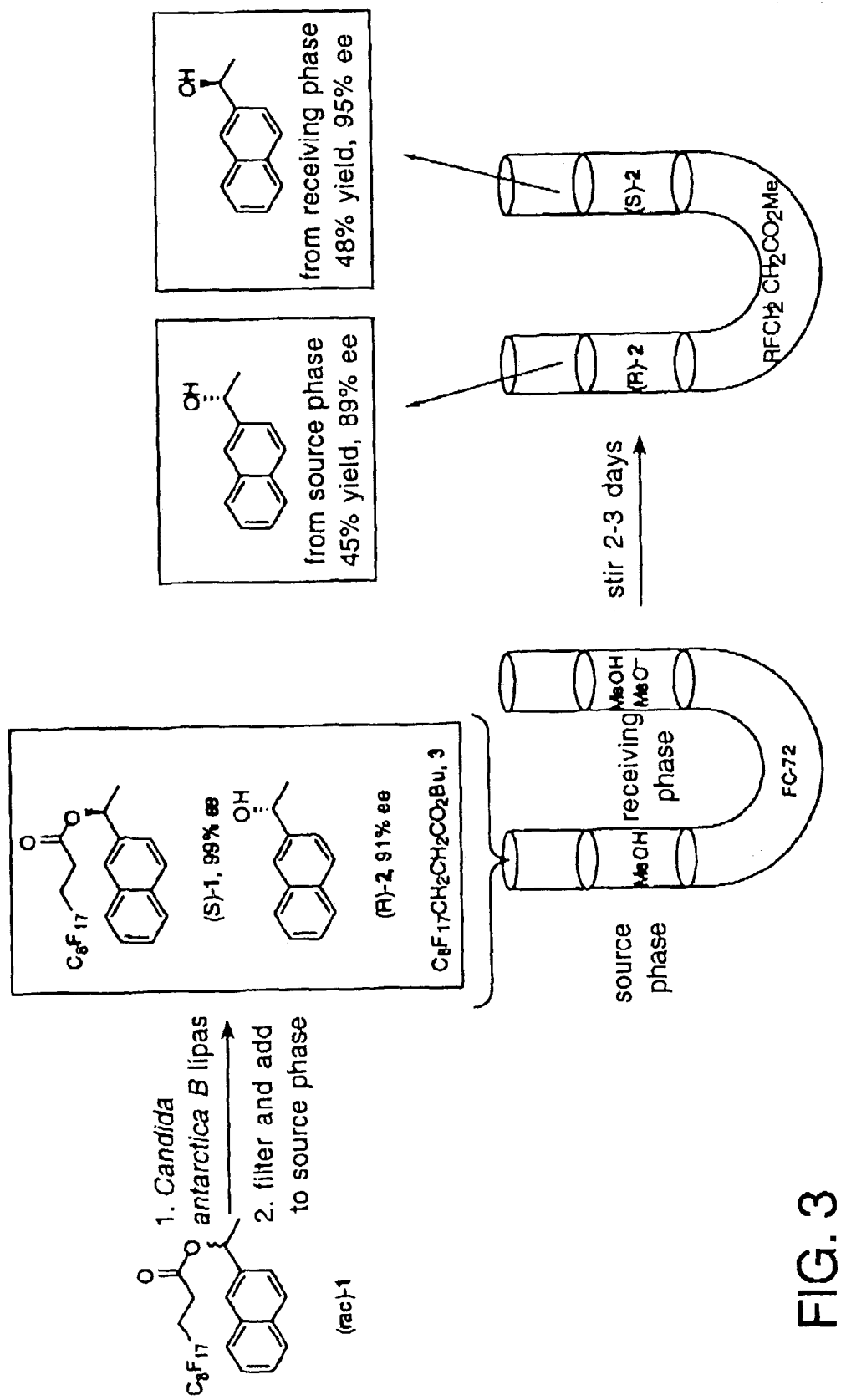
FIG. 3 is a schematic diagram of the resolution of racemic 2-naphthylethanol by kinetic resolution and triphasic separation/reaction.

The resolution of racemic 2-naphthylethanol is representative of one method by which alcohols may be resolved. This is an example of the detagging approach using a lipase enzyme to effect the enantioselective detagging. Sodium methoxide is the cleavage reagent in the non-fluorous receiving side. Racemic ester 1 was readily prepared by acylation of 1-(2-napthyl)ethanol with 2H,2H,3H,3H-perfluoroundecanoyl chloride. The process that resolves (rac)-1 into (S)-1 and (R)-2 is shown in FIG. 3.

The kinetic resolution of fluorous ester rac-1 was conducted with *Candida antarctica* B lipase and the reaction was stopped when the conversion reached about 50%. The lipase was removed by filtration, and the resulting crude mixture containing ester (S)-1 and alcohol (R)-2 was used for the fluorous triphasic reaction. A related mixture can be generated by enzymatic tagging of the racemic alcohol; see, B. Hungerhoff, H. Sonnenschein, F. Theil, "Separation of enantiomers by extraction based on lipase-catalyzed enantiomer-selective fluorous-phase labeling," *Angew. Chem., Int. Ed. Eng.*, 40, 2492 (2001). In a control experiment, ester 1 and alcohol 2 were separated by silica gel column chromatography to give (R)-2 in 50% yield with >99% ee. Saponification of ester (S)-1 with NaOMe gave alcohol (S)-2 in 50% yield with 91% ee.

In a typical triphasic experiment, a U-tube was charged with FC-72 (perfluorohexanes), and the mixture obtained from the kinetic resolution was added to the source phase (MeOH/CHCl$_3$). A solution of NaOMe/MeOH made up the receiving phase. All three phases were gently stirred at room temperature for 3 days. Evaporation of the source phase gave alcohol (R)-2 with 95±1% ee. Workup of the receiving phase provided (S)-2 with 89±2% ee. The yields of (R)-2 and (S)-2 were comparable to those obtained from silica gel column chromatography followed by saponification (45% and 48% respectively). Methyl (3-perfluorooctyl)propionate was isolated from the FC-72 phase.

Chiral primary and secondary amines can be resolved by substantially similar methods by using tagging and detagging chemistry that is suitable for amines and their derivatives. Mixtures of tagged and untagged enantiomers can be generated by either enantioselective chemical or enzymatic reactions such as acylations and the like. And the amide, urethane, carbamate, urea and related derivatives can be cleaved on the receiving side by standard reactions.

Figure 4:
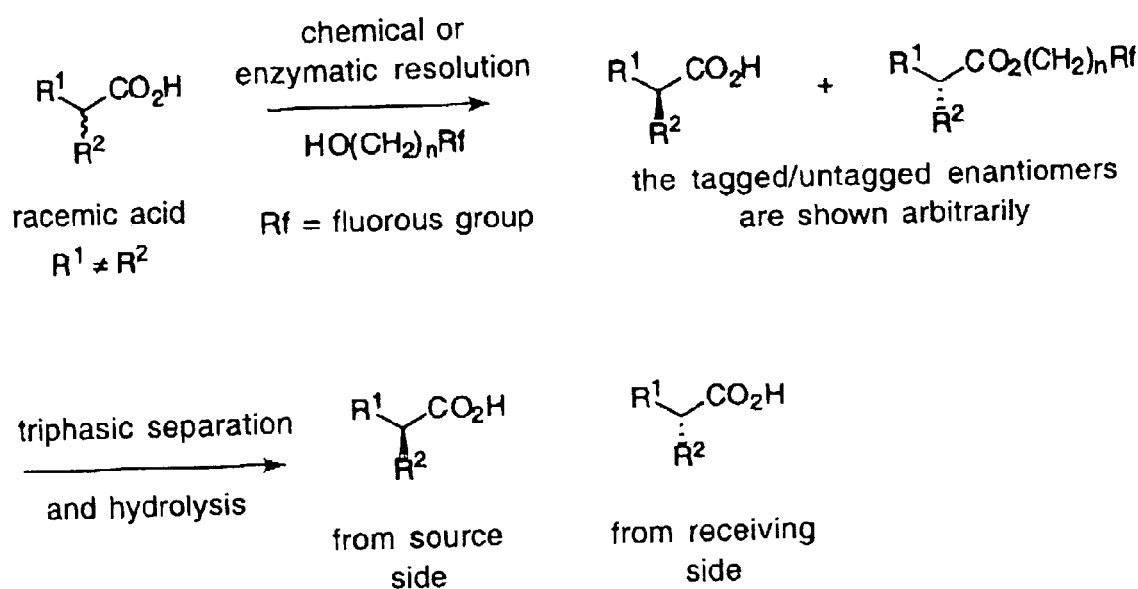
FIG. 4 is a series of chemical reaction diagrams showing the kinetic resolution and triphasic separation/reaction of a chiral carboxylic acid with a fluorous alcohol tag.

For resolutions of chiral carboxylic acids and carboxylic acid derivatives, the roles of the fluorous and the non-fluorous components in the tagging process are simply reversed. Now the carboxylic acid or its derivative is a non-fluorous component and the amine, alcohol or a suitable derivative (for example, a silylated, stannylated or metallated amine or alcohol) is the fluorous tagging component. FIG. 4 provides an example of the resolution of a typical carboxylic acid with a fluorous alcohol.

Among the many types of compounds that can be resolved by this invention, amino acids are especially important. These can be resolved either by attaching a fluorous tag to the amine functionality or the acid functionality.

EXAMPLE 1

Kinetic Resolution of rac-1: A solution of the racemic ester rac-1 (5 mmol) in acetonitrile (120 mL) was treated with n-butanol (20 mmol) and *Candida antarctica* B lipase (Chirazyme L-2, c.-f., lyo. from Roche Diagnostics, Mannheim) (8.0 g). The reaction mixture was stirred at ambient temperature until the conversion reached ca. 50% (estimated by TLC, 7 days). The lipase was removed by filtration and washed with acetone (2×40 mL). The combined filtrates were evaporated under reduced pressure to provide a mixture of ester (S)-1, alcohol (R)-2 and butyl ester 3 (butyl 2H,2H,3H,3H-perfluoroundecanoate). An aliquot of this mixture (116 mg) was purified by silica gel column chromatography (15%–30% EtOAc/hexane) to give alcohol (R)-2 (16.0 mg, 50% yield, >99% ee) and ester (S)-1 (60 mg). Treatment of (S)-1 with NaOMe/MeOH at room temperature for 30 min to give (S)-2 (15 mg, 50% yield, 91% ee). The ee of (S)-2 and (R)-2 were determined by chiral HPLC (column: Chiralcel OJ, eluent: n-hexane/2-propanol (9:1), flow rate: 1 mL/min, UV-detection at 254 nm).

EXAMPLE 2

Fluorous Triphasic Reaction: To a U-shape tube charged with FC-72 (15 ml) was added a solution of the mixture of ester (S)-1, alcohol (R)-2 and butyl ester 3 (116 mg) in MeOH/CHCl$_3$ (6 ml, 5:1) to the substrate side and NaOMe (0.2 ml, 25% wt in MeOH) in MeOH (6 ml) to the reagent side. All three phases were gently stirred at room temperature for 72 h. The source phase was taken up with a pipette and evaporated to dryness. The residue was passed through a silica plug with 25% EtOAc/Hexanes to give (R)-2 (13 mg, 45% yield, 95±1% ee). The receiving phase was taken up and added to 1N aq. HCl. After extraction with diethyl ether, the ether layer was dried over magnesium sulfate and evaporated to dryness. The residue was passed through a silica plug with 25% EtOAc/Hexanes to give (S)-2 (14 mg, 48% yield, 89±2% ee). The % ee was determined by chiral HPLC as mentioned above and was reported as an average of the results from two triphasic reaction experiments.

The invention claimed is:

1. A method of obtaining an enantioenriched organic compound comprising the steps of:
   generating from a starting racemic, non-enantiopure or achiral compound a first mixture comprising at least one fluorous-tagged compound and at least one other non-fluorous tagged compound, at least one of these two compounds being enantioenriched relative to the starting compound;
   contacting a first non-fluorous phase including the first mixture with a fluorous phase at a first phase interface, the fluorous-tagged compound distributing between the first non-fluorous phase and the fluorous phase; and
   contacting the fluorous phase with a second non-fluorous phase at a second phase interface.

2. The method of claim 1 including at least a third compound in the second non-fluorous phase that reacts with the fluorous-tagged compound to produce a second compound, the second compound having a distribution coefficient less than the fluorous-tagged compound.

3. The method of claim 1 including the step of generating the first mixture by chemical or enzymatic kinetic resolution of a racemic or non-enantiopure chiral alcohol, amine, carboxylic acid or carboxylic acid derivative.

4. The method of claim 3 including at least a third compound in the second non-fluorous phase that reacts with the fluorous-tagged compound to produce a second compound, the second compound having a distribution coefficient less than the fluorous-tagged compound.

5. The method of claim 2 wherein the second compound is an alcohol, amine, carboxylic acid or carboxylic acid derivative precursor of the fluorous-tagged compound.

6. The method of claim 3 wherein the first mixture is generated in the first non-fluorous phase.

7. The method of claim 1 wherein at least one of the first non-fluorous phase and the second non-fluorous phase is an aqueous phase.

8. The method of claim 1 wherein at least one of the first non-fluorous phase and the second non-fluorous phase is an organic phase.

9. The method of claim 1 wherein the fluorous-tagged compound has a distribution coefficient between the first organic phase and the fluorous phase between approximately 0.01 and approximately 10.

10. The method of claim 2 wherein a fluorous compound resulting from the reaction of the fluorous-tagged enantiomer and the third compound distributes preferentially from the second non-fluorous phase into the fluorous phase.

11. The method of claim 1 wherein the first mixture comprises an alcohol and an ester.

12. The method of claim 1 wherein the first mixture comprises an amine and an amide.

13. The method of claim 1 wherein the first mixture comprises a carboxylic acid and an ester or amide.

14. The method of claim 1 wherein the first mixture comprises two carboxylic acid derivatives, one of which is fluorous-tagged.

15. The method of claim 1 further comprising the step of contacting the second non-fluorous phase with a second fluorous phase at a third phase interface.

16. The method of claim 15 further comprising the step of contacting the second fluorous phase with a third non-fluorous phase at a fourth phase interface.

17. The method of claim 2 wherein at least one of the first non-fluorous phase and the second non-fluorous phase is an organic phase.

18. The method of claim 2 wherein the fluorous-tagged compound has a distribution coefficient between the first organic phase and the fluorous phase between approximately 0.01 and approximately 10.

19. The method of claim 2 wherein the first mixture comprises an alcohol and an ester.

20. The method of claim 2 wherein the first mixture comprises an amine and an amide.

21. The method of claim 2 wherein the first mixture comprises a carboxylic acid and an ester or amide.

22. The method of claim 2 wherein the first mixture comprises two carboxylic acid derivatives, one of which is fluorous-tagged.

23. The method of claim 4 wherein at least one of the first non-fluorous phase and the second non-fluorous phase is an organic phase.

24. The method of claim 4 wherein the fluorous-tagged compound has a distribution coefficient between the first organic phase and the fluorous phase between approximately 0.01 and approximately 10.

25. The method of claim 4 wherein a fluorous compound resulting from the reaction of the fluorous-tagged enantiomer and the third compound distributes preferentially from the second non-fluorous phase into the fluorous phase.

26. The method of claim 4 wherein the first mixture comprises an alcohol and an ester.

27. The method of claim 4 wherein the first mixture comprises an amine and an amide.

28. The method of claim 4 wherein the first mixture comprises a carboxylic acid and an ester or amide.

29. The method of claim 4 wherein the first mixture comprises two carboxylic acid derivatives, one of which is fluorous-tagged.

* * * * *